(12) United States Patent
Arzegar

(10) Patent No.: US 10,413,376 B2
(45) Date of Patent: Sep. 17, 2019

(54) DENTAL DEVICE

(71) Applicant: Reza Arzegar, Austin, TX (US)

(72) Inventor: Reza Arzegar, Austin, TX (US)

( * ) Notice: Subject to any disclaimer, the term of this patent is extended or adjusted under 35 U.S.C. 154(b) by 33 days.

(21) Appl. No.: 15/609,086

(22) Filed: May 31, 2017

(65) Prior Publication Data

US 2017/0258541 A1 Sep. 14, 2017

Related U.S. Application Data

(62) Division of application No. 14/873,044, filed on Oct. 1, 2015, now abandoned.

(60) Provisional application No. 62/086,871, filed on Dec. 3, 2014.

(51) Int. Cl.
*A61B 42/20* (2016.01)
*A61C 5/90* (2017.01)

(52) U.S. Cl.
CPC .............. *A61B 42/20* (2016.02); *A61C 5/90* (2017.02)

(58) Field of Classification Search
CPC ........... A61B 42/20; A61B 42/00; A61B 1/24; A41D 19/0055; A41D 13/687; A41D 2400/80; A41D 13/00; A61F 13/105; A61F 13/104; A61F 2006/048; A61F 5/50; A61F 13/10; D05B 91/04; A61J 17/02; A61J 17/001; A61D 13/087; A61D 15/00; A61C 5/90; B42D 9/04; A46B 5/04
USPC ........................... 433/140, 136; 2/21; 294/25; 128/879–880; 223/101
See application file for complete search history.

(56) References Cited

U.S. PATENT DOCUMENTS

| | | | | |
|---|---|---|---|---|
| 128,093 A * | 6/1872 | Allerton | ........................ | 15/188 |
| 490,733 A * | 1/1893 | Armat | .................. | A41D 13/087 128/880 |
| 540,975 A * | 6/1895 | Grimes | .................... | D05B 1/04 2/21 |
| 911,838 A * | 2/1909 | Napier | .................. | A61F 13/105 2/21 |
| 2,379,624 A * | 7/1945 | Chisnell | ................ | A61F 13/105 15/227 |
| 2,512,872 A * | 6/1950 | Penksa | .................. | A61B 42/20 2/21 |
| 2,742,898 A * | 4/1956 | Beaudry | .................... | A61F 5/50 128/880 |
| 3,043,295 A * | 7/1962 | Ward | ....................... | A46B 1/00 15/110 |
| 4,308,860 A * | 1/1982 | Sanders | .................... | A46B 1/00 15/227 |
| 4,852,586 A * | 8/1989 | Haines | .................... | A61F 6/04 128/842 |
| 5,450,626 A * | 9/1995 | Sorrels | ............. | A41D 19/01517 2/163 |
| 5,496,337 A * | 3/1996 | Brown | ............... | A61B 17/0493 2/161.7 |

(Continued)

*Primary Examiner* — Wade Miles
*Assistant Examiner* — Shannel N Wright
(74) *Attorney, Agent, or Firm* — Pierson IP, PLLC

(57) ABSTRACT

Embodiments disclosed herein describe systems and methods for a dental device that is configured to be worn on a user's finger, and inserted into the mouth of a patient. The dental device may be comprised of rigid and/or semi-rigid materials, wherein when dental device is inserted between an upper set and lower set of the patient's teeth, the dental device may maintain the patient's mouth in an open position.

4 Claims, 14 Drawing Sheets

(56) References Cited

U.S. PATENT DOCUMENTS

| | | | | |
|---|---|---|---|---|
| 5,664,946 | A * | 9/1997 | Bedi | A61B 1/24 |
| | | | | 433/140 |
| 5,765,252 | A * | 6/1998 | Carr | A46B 5/04 |
| | | | | 15/104.94 |
| 6,027,511 | A * | 2/2000 | Shirley | A61B 42/20 |
| | | | | 606/119 |
| 6,110,186 | A * | 8/2000 | Rizvi | A61B 17/0493 |
| | | | | 128/846 |
| 6,237,148 | B1 * | 5/2001 | Graham | A41D 13/087 |
| | | | | 2/21 |
| 6,839,905 | B1 * | 1/2005 | Bruder | A41D 13/087 |
| | | | | 2/21 |
| 7,066,735 | B1 * | 6/2006 | Gasporra | A61C 5/90 |
| | | | | 433/140 |
| 9,439,461 | B1 * | 9/2016 | Hall | A41D 13/087 |
| 2002/0152538 | A1 * | 10/2002 | McDevitt | A41D 13/087 |
| | | | | 2/163 |
| 2007/0118947 | A1 * | 5/2007 | Lorenzo | A41D 13/087 |
| | | | | 2/21 |
| 2008/0018123 | A1 * | 1/2008 | Cox | A61F 13/10 |
| | | | | 294/25 |
| 2009/0005810 | A1 * | 1/2009 | Bonazza | A61J 17/02 |
| | | | | 606/235 |
| 2012/0016416 | A1 * | 1/2012 | Frazier | A61J 17/02 |
| | | | | 606/235 |
| 2012/0222186 | A1 * | 9/2012 | Vena | A41D 13/087 |
| | | | | 2/21 |
| 2013/0245687 | A1 * | 9/2013 | Bachmann | A61J 17/02 |
| | | | | 606/235 |
| 2016/0015161 | A1 * | 1/2016 | Mullen | A46B 5/04 |
| | | | | 433/216 |

* cited by examiner

DENTAL DEVICE

CROSS-REFERENCE TO RELATED APPLICATIONS

This application claims a benefit of priority under 35 U.S.C. § 119 to Provisional Application No. 62/086,871 filed on Dec. 3, 2014, which is fully incorporated herein by reference in its entirety.

BACKGROUND INFORMATION

Field of the Disclosure

Examples of the present disclosure are related to dental devices. More specifically, embodiments are directed towards systems and methods for adults to assist in properly brushing children's teeth.

Background

A common complaint among parents of infants is not being able to properly brush their infant's teeth. The inability for parents' inability to brush their infant's teeth stems from infants having a tendency to close their mouth and bite down on a toothbrush while the parent is brushing their teeth. This leaves an immobile toothbrush within the infant's mouth. This issue is not only isolated to infants, but to any animal.

If proper dental care is not administered to infant's teeth, tooth decay is more likely to become an issue for these individuals later in life. Tooth decay is a major disease threatening oral health amount children in the United States, as well as adults. Tooth decay, which can be prevents and/or limited, leads to excessive pain and may force children to miss school for emergency dental care.

Accordingly, needs exist for dental devices that are configured to be worn on a finger of an adult to maintain an infant's jaw in an open position when the adult is brushing the teeth of the infant.

SUMMARY

Embodiments disclosed herein describe systems and methods for a dental device configured to be worn on a user's finger, and inserted into the mouth of a patient, wherein the patient may be an infant, adult, animal, etc. The dental device may be configured to be placed over a finger of the user, and the user may place their finger covered by the dental device into the patient's mouth. When the patient's mouth is open, the user may place the finger covered by the device between the patient's upper set and lower set of teeth. The patient may then naturally clench or close their teeth, clenching down on the dental device. However, due to the rigidity of the dental device, the patient may not be able to closer their jaw, enabling the user to begin brushing the teeth of the patient.

In embodiments, the user may adjust a placement of the dental device within the patient's mouth as desired. If the user desires more control over the jaw of the patient, the user may take the patient's head and gently place the side of the head of the patient's on the user's lap.

In embodiments, the dental device may be comprised of materials that are safe to be put within the patient's or an infant's mouth. Additionally, the dental device may be configured to provide support, protection, etc. for the user's finger, while the user's finger is within the patient's mouth. The dental device may be comprised of rubber-like materials that are harder than conventional finger toothbrushes, but not hard enough to injure in infant's teeth, gums, or mouths. The materials may be solid, rigid, or semi-rigid materials that an individual cannot bite through.

In embodiments, an exterior surface of the dental device may include a plurality of projections, ridges, bumps, etc. The plurality of projections may be configured to assist in securing the dental device within the patient's mouth.

In embodiments, an interior surface of the dental device may have tapered or slanted sidewalls, wherein the tapered sidewalls may assist in securing the dental device on the user's finger.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
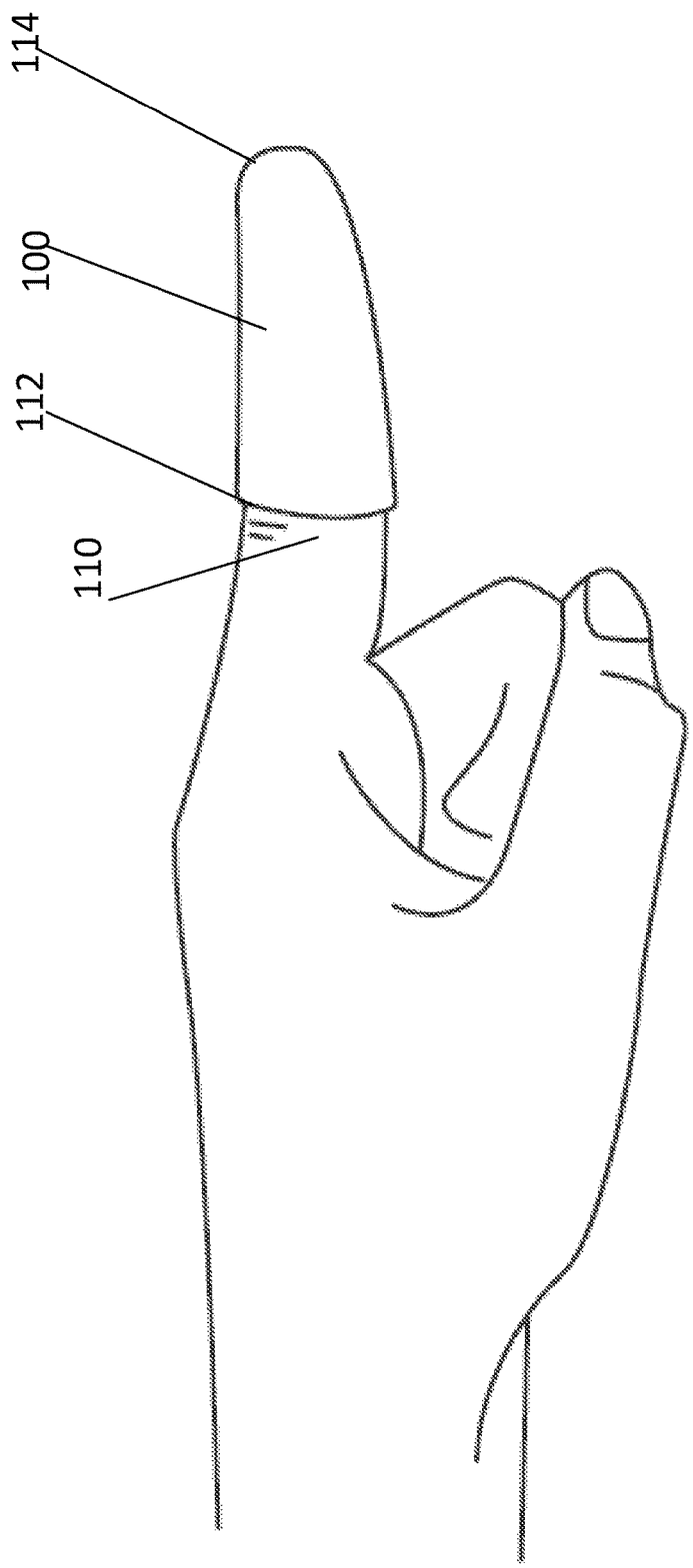
FIG. 1 depicts a dental device on a user's finger, according to an embodiment.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

Embodiments disclosed herein describe systems and methods for a dental device that is configured to be worn on a user's finger, and inserted into the mouth of a patient. The dental device may be comprised of rigid and/or semi-rigid materials, wherein when dental device is inserted between an upper set and lower set of the patient's teeth, the dental device may maintain the patient's mouth in an open position.

FIG. 1 depicts a dental device 100 configured to be worn on a user's finger 110, according to one embodiment.

Dental device 100 may be comprised of a thin casing that is configured to cover a finger 110 of a user. Dental device 100 may include a first end 112 and a second end 114.

First end 112 may include an orifice configured to receive the finger 110 of the user, and second end 114 may include a rounded edge. The interior surface of dental device 100 may include a hollow chamber extended from first end 112 to second end 114. The exterior surface of dental device 100 may be cylindrical in shape that narrows towards the second end 114 of dental device 100.

Dental device 100 configured to be worn on finger 110. In operation, a user may slide a first end 112 of dental device 100 over a distal end of their finger 110 until the distal end of finger 110 is proximate to second end 114 of dental device 100. Responsive to dental device 100 being positioned over the distal end of finger 110, finger 110 may be inserted into the mouth of a patient. When the patient opens their mouth, dental device 100 may be inserted between the patient's upper set and lower set of teeth. The patient may then naturally clench or close their teeth, clenching down on dental device 100. Due to the rigidity of dental device 100, the user may then begin brushing the teeth of the patient.

By having dental device 100 being worn on finger 110, the user may efficiently and effectively control the placement of dental device 100 within the patient's mouth. In embodiments, the user may adjust a placement of dental device 100 within the patient's mouth as desired. If the user desires more control over the jaw of the patient, the user may take the patient's head and gently place the side of the head of the patient's on the user's lap.

In embodiments, dental device 100 may be comprised of rigid and/or semi-rigid materials, wherein when the patient clenches their teeth the shape of dental device 100 may not change. Accordingly, while dental device 100 is on the user's finger and between the patient's teeth, the distance between the patient's lower set of teeth and upper set of teeth may be at least as wide as the fixed diameter of dental device 100. Thus, the rigidity of dental device 100 may allow the user to efficiently and effectively brush the teeth of the patient.

In embodiments, dental device 100 may have a length that is configured to cover the distal phalange, intermediate phalange, and portions of the proximal phalange of finger 110. Therefore, when dental device 100 is positioned over finger 110, the middle phalanx of the user's finger 110 may remain straightened. In embodiments, the height of dental device 100 may be one to one and a half inches, and have a thickness of two to three millimeters. However, persons skilled in the art will appreciate that dental device 100 may be formed in different shapes and/or sizes to accommodate a variety of finger sizes and mouth sizes. The diameter of dental device 100 may be substantially similar to the diameter of finger 110. However, different embodiments of dental device 100 may have varying diameters.

In embodiments, an exterior surface of dental device 100 may include a plurality of projections, ridges, bumps, etc. The plurality of projections may be configured to assist in securing the dental device within the patient's mouth. In embodiments, an interior surface of the dental device 100 may have tapered or slanted sidewalls, wherein the tapered sidewalls may assist in securing the dental device on the user's finger.

Figure 2:
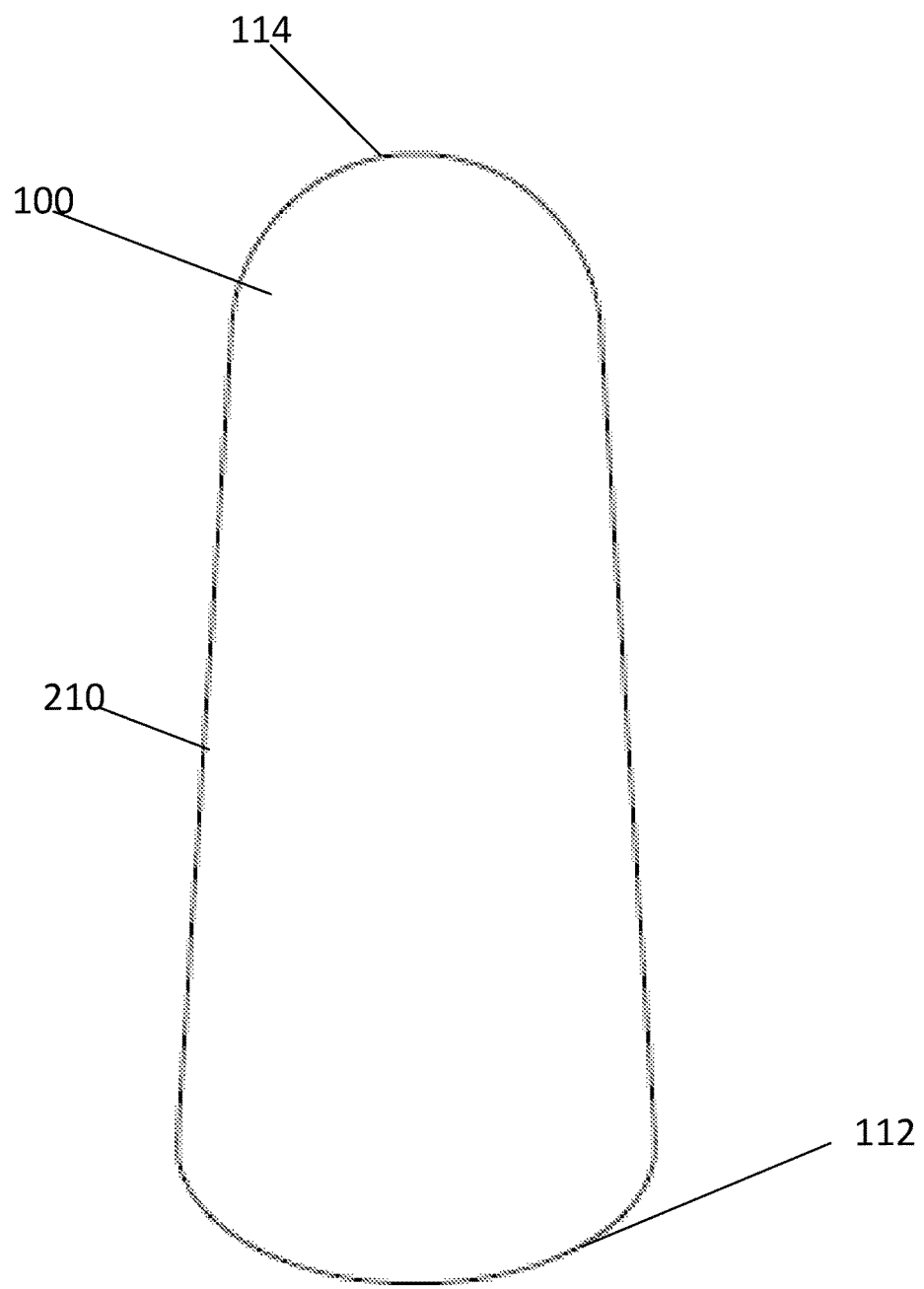
FIG. 2 depicts a front view of a dental device, according to an embodiment.

FIG. 2 depicts a front view of dental device 100, according to an embodiment. As depicted in FIG. 2, dental device 100 may have tapered sidewalls 210. Tapered sidewalls 210 may decrease the circumference of dental device 100 from first end 112 to second end 114. Accordingly, first end 112 may have a greater circumference than second end 114.

Furthermore, as depicted in FIG. 2, second end 114 may have a rounded face. The rounded face of second end 114 may enable a distal end of dental device 100 to not have any sharp edges, which may increase the comfort of a patient when dental device 100 to be move comfortable positioned within a patients mouth.

Figure 3:
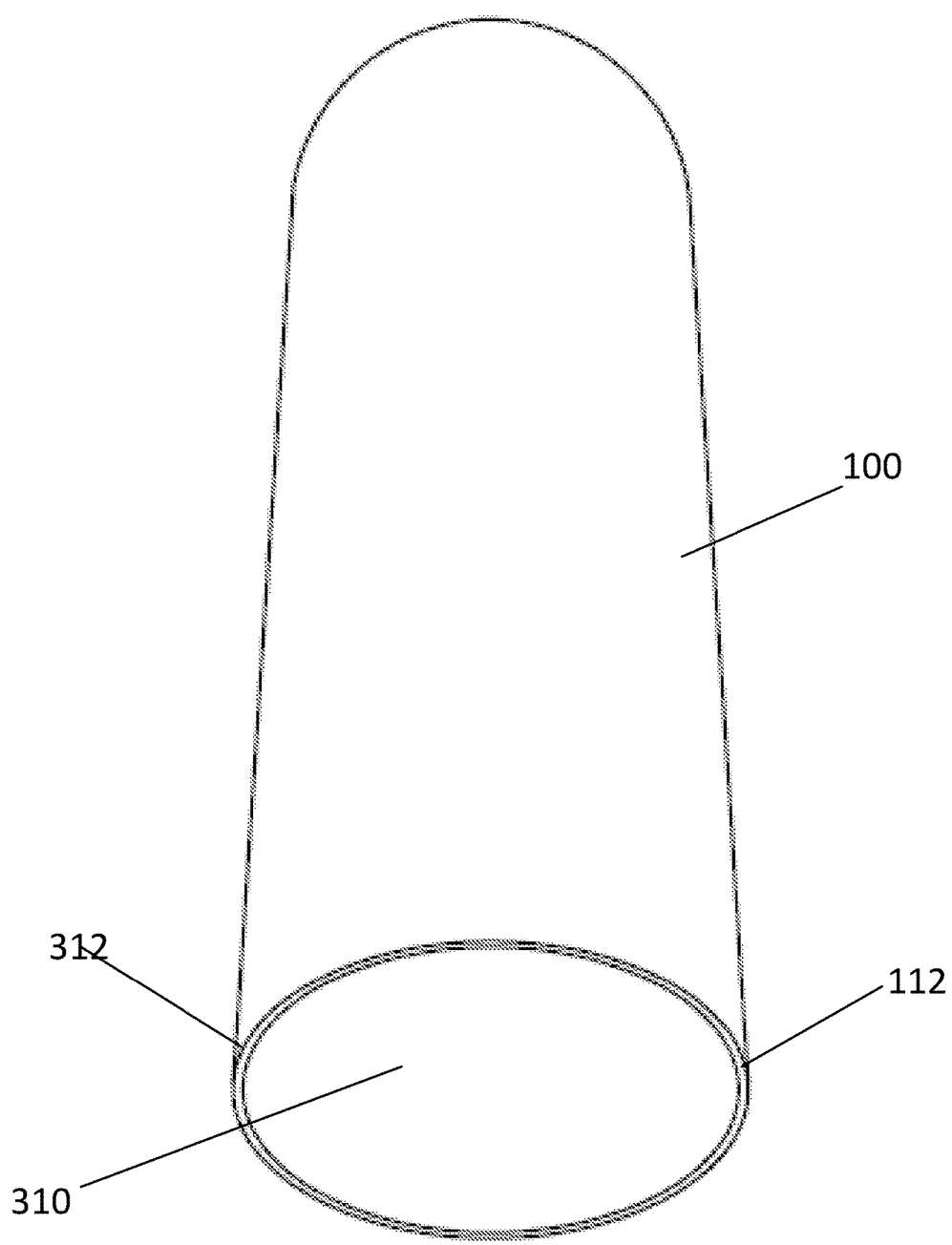
FIG. 3 depicts a bottom perspective view of a dental device, according to an embodiment.

FIG. 3 depicts a perspective view of dental device 100, according to an embodiment.

As depicted in FIG. 3, first end 112 of dental device 100 may have an opening 310 that forms a hollow chamber within dental device 100. The opening 310 may extend from the first end 112 of dental device 100 to second end 114 of dental device 100. Opening 310 may be configured to receive the finger of the user, and tapered, interior sidewalls 312 may be configured to secure dental device 100 on the finger of the user.

Figure 4:
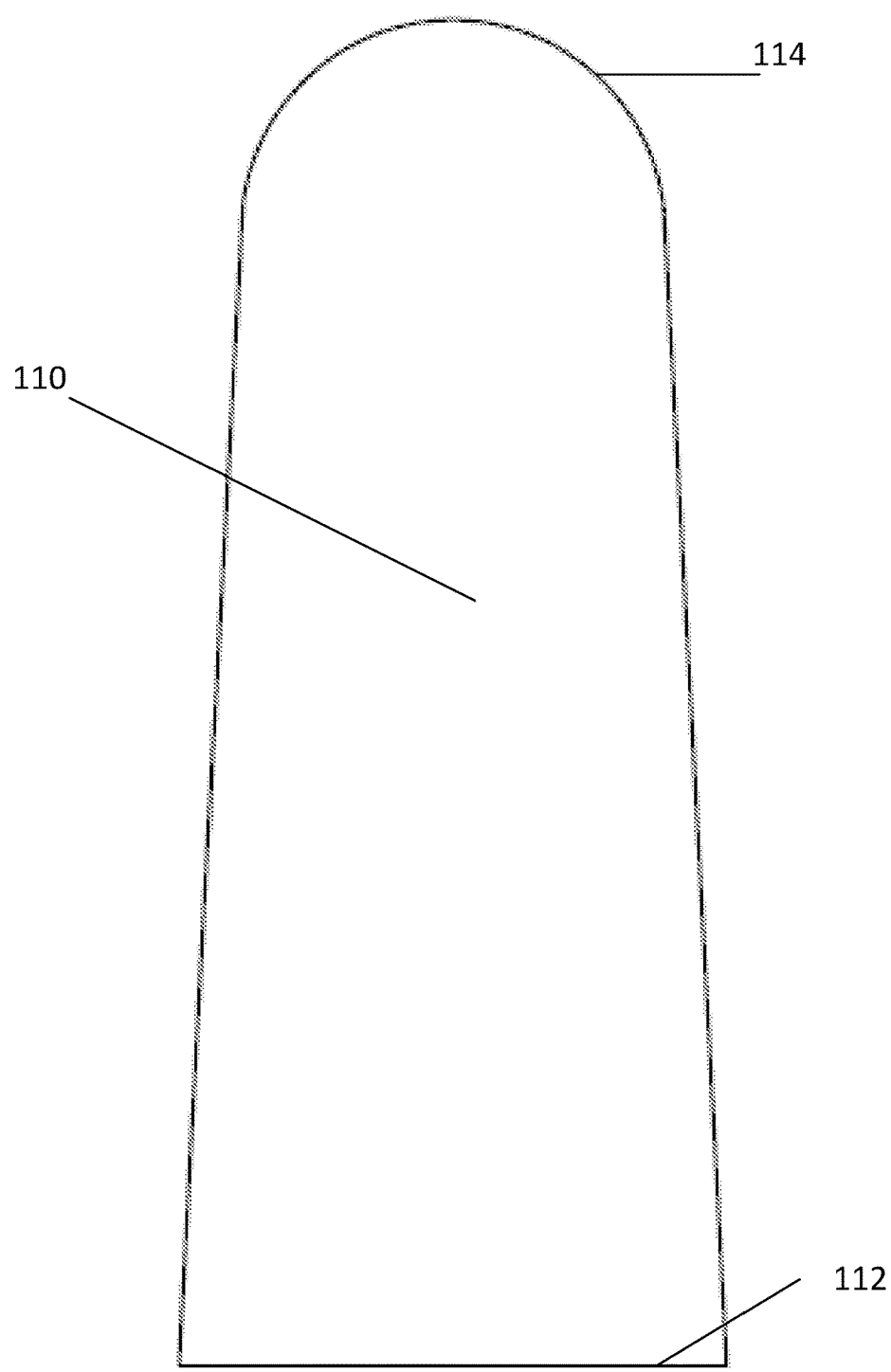
FIG. 4 depicts a back view of a dental device, according to an embodiment.
Figure 5:
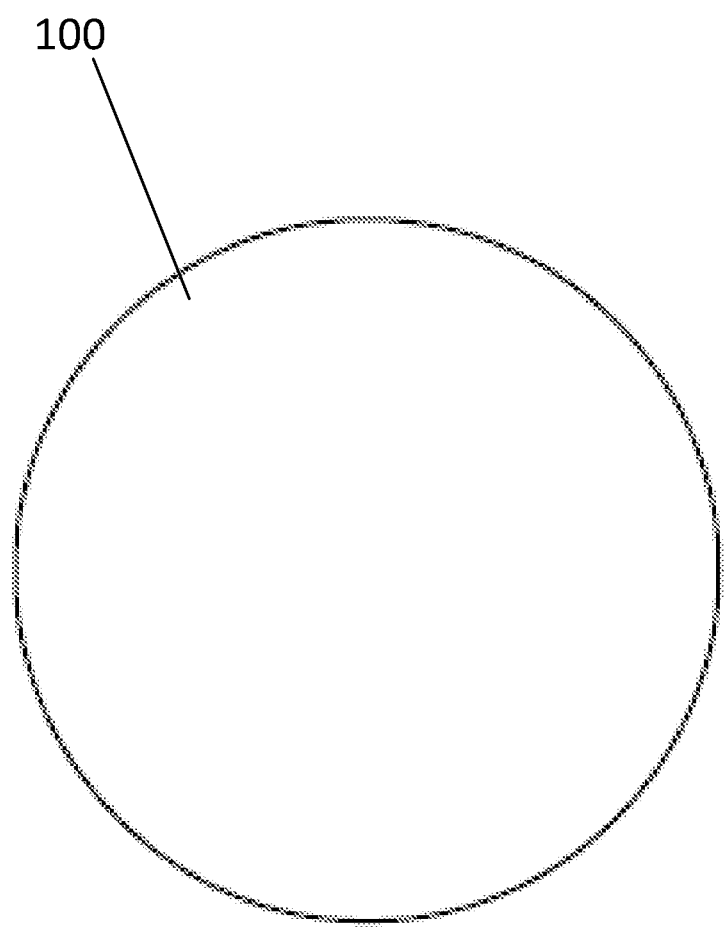
FIG. 5 depicts a top view of a dental device, according to an embodiment.
Figure 6:
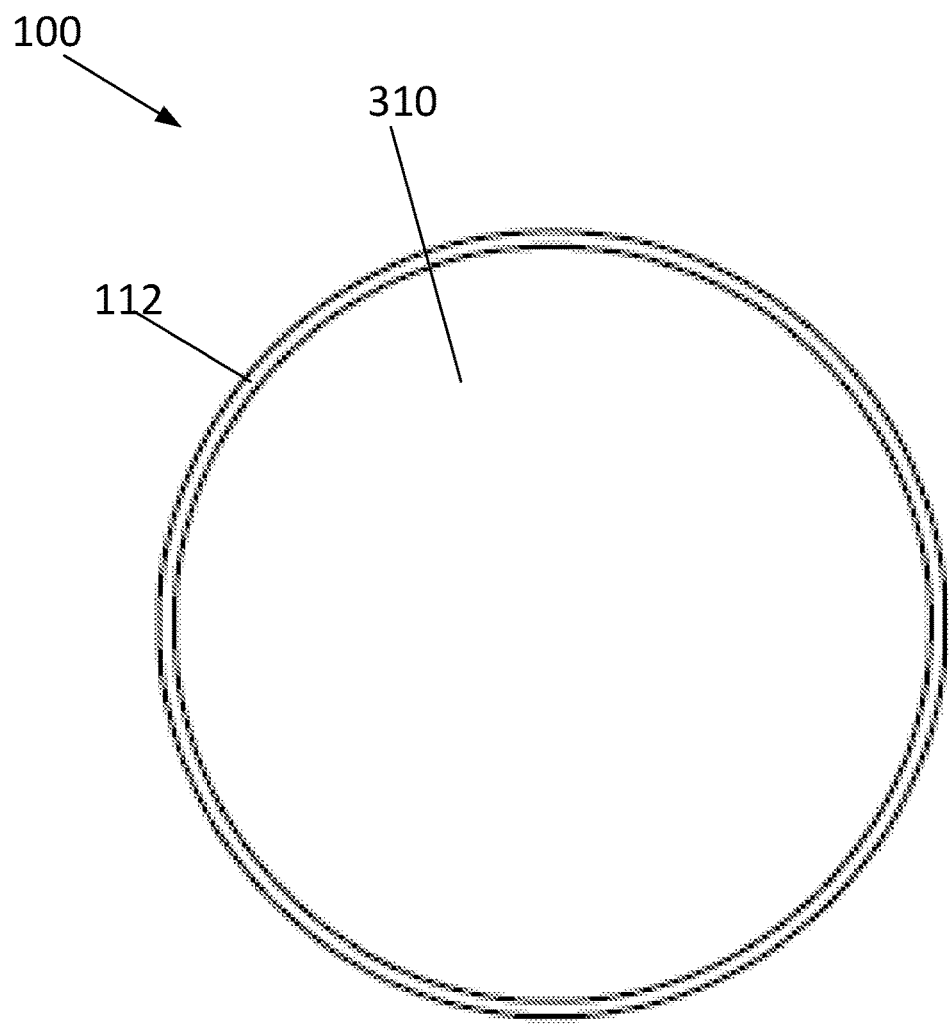
FIG. 6 depicts a bottom view of a dental device, according to an embodiment.

FIG. 4 depicts a side view of dental device 100, according to an embodiment. FIG. 5 depicts a top view of dental device 100, according to an embodiment. FIG. 6 depicts a bottom view of dental device 100, according to an embodiment.

Figure 7:
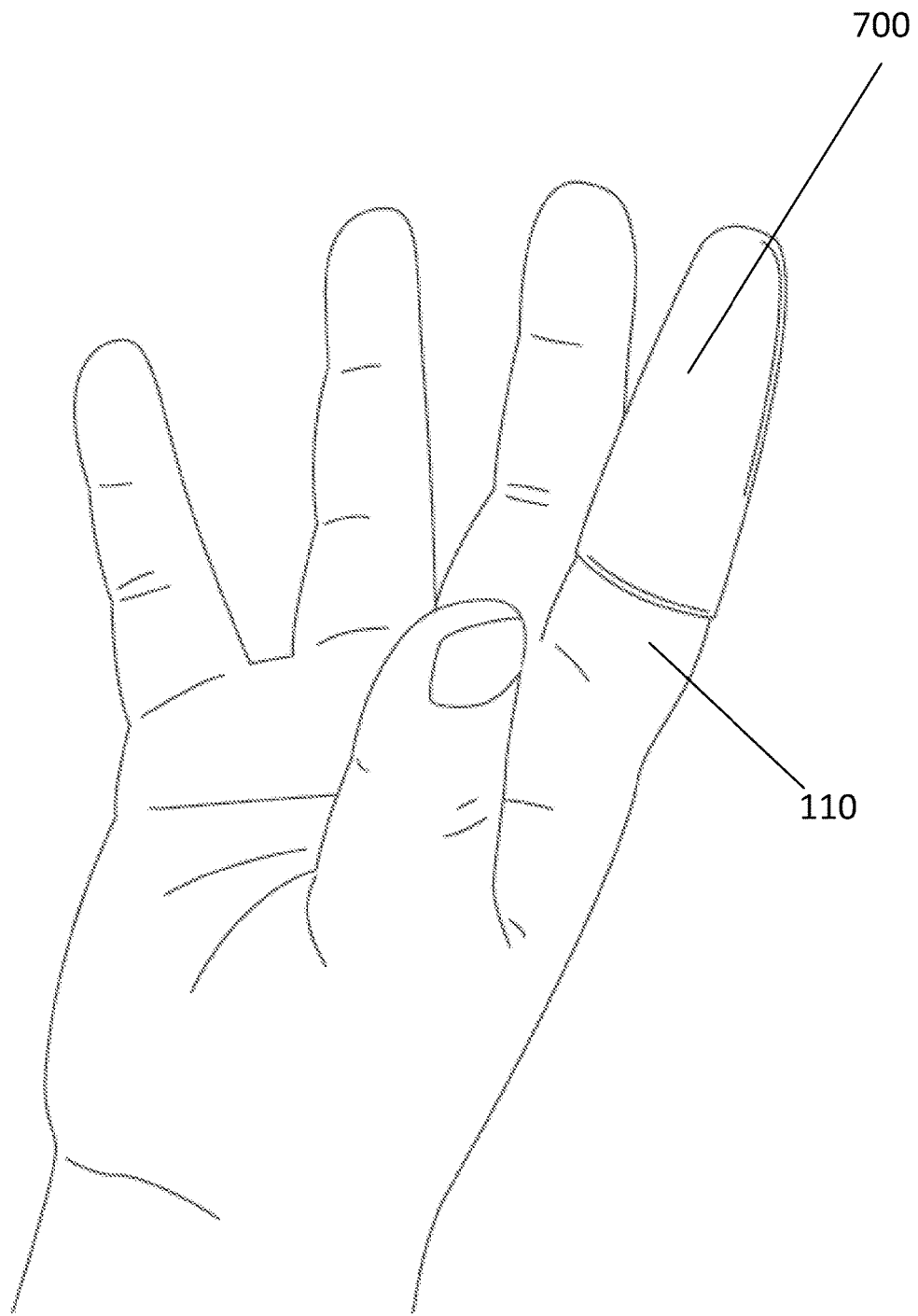
FIG. 7 depicts a dental device on a user's finger, according to an embodiment.

FIG. 7 depicts a dental device 700, according to an embodiment. As depicted in FIG. 7 dental device 700 may have a length that is configured to cover both distal phalanx joint and the proximal phalanx joint. Accordingly, when dental device 700 is positioned over a finger 110 of the user, the rigidity of dental device 700 may force the user's finger 110 to be straightened.

Figure 8:
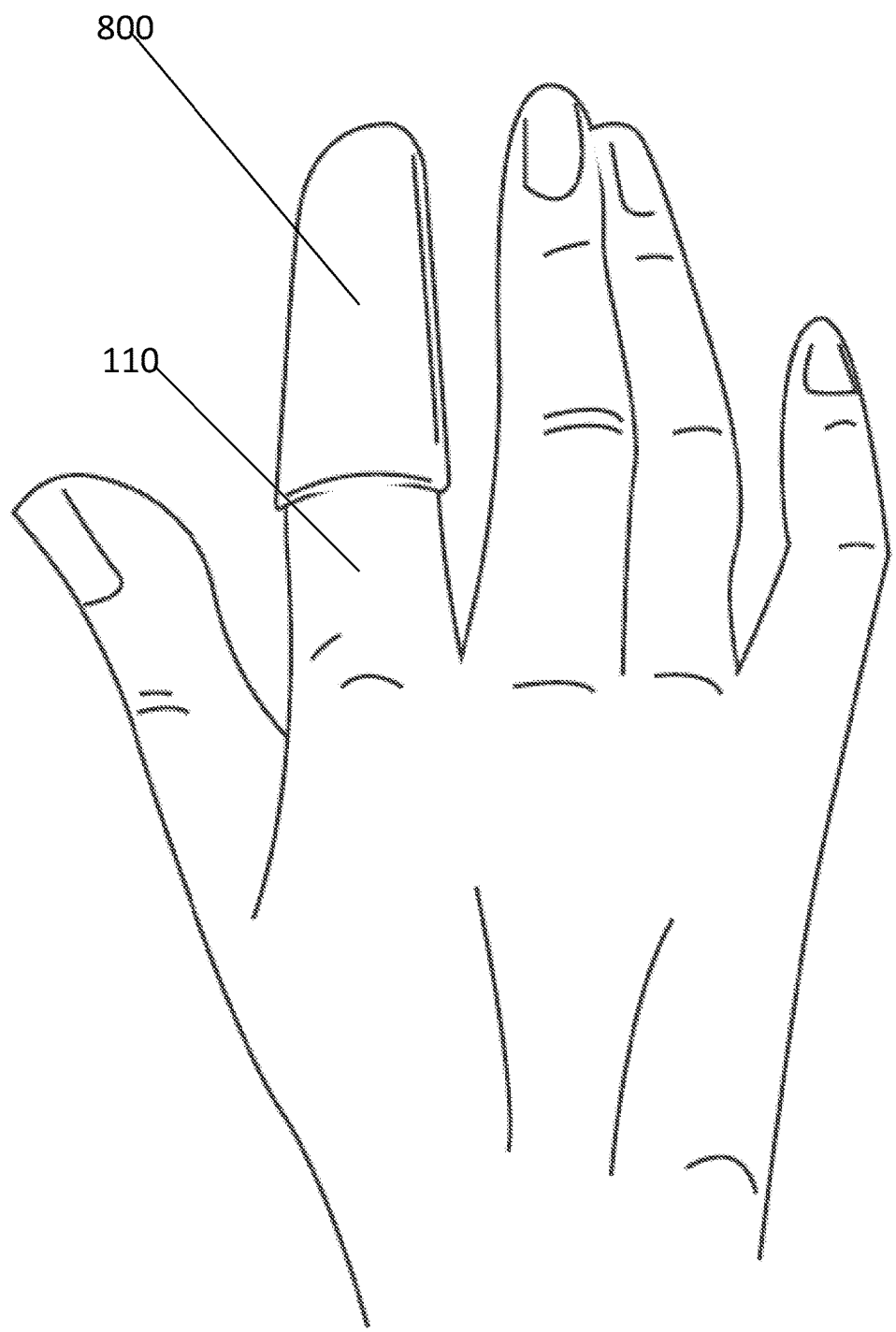
FIG. 8 depicts a dental device on a user's finger, according to an embodiment.

FIG. 8 depicts a dental device 800, according to an embodiment. As depicted in FIG. 7 dental device 800 may have a length that is configured to the distal phalanx joint of the user's finger 110.

Figure 9:
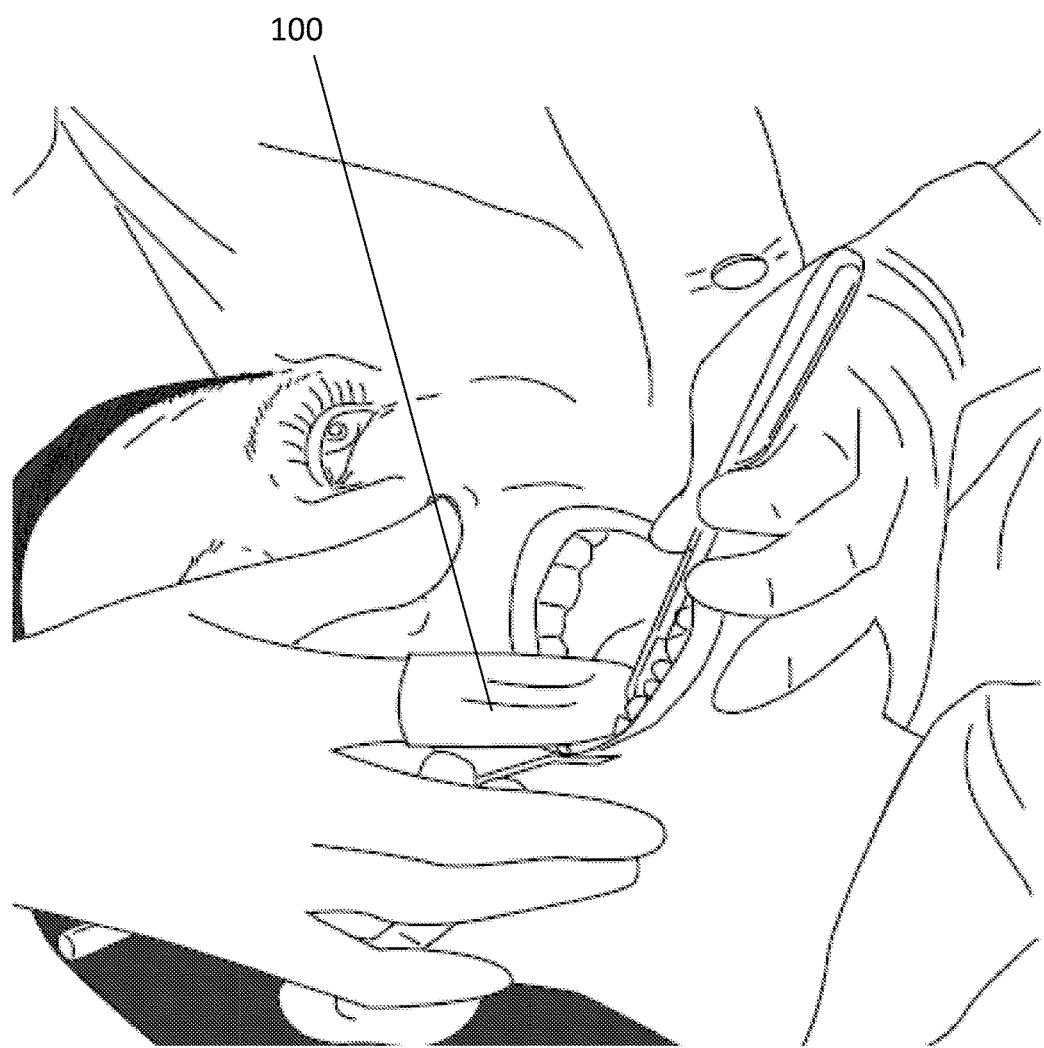
FIG. 9 depicts a dental device in use, according to an embodiment.

FIG. 9 depicts one embodiment of dental device 100 in use, according to an embodiment. As depicted in FIG. 9, dental device 100 may be positioned on a user's finger, and inserted into the mouth of a patient. Based on the angle of insertion into the patient's mouth, the patient's jaw may remain opened. While the patient's jaw is opened, the user may perform dental care on the patient.

Figure 10:
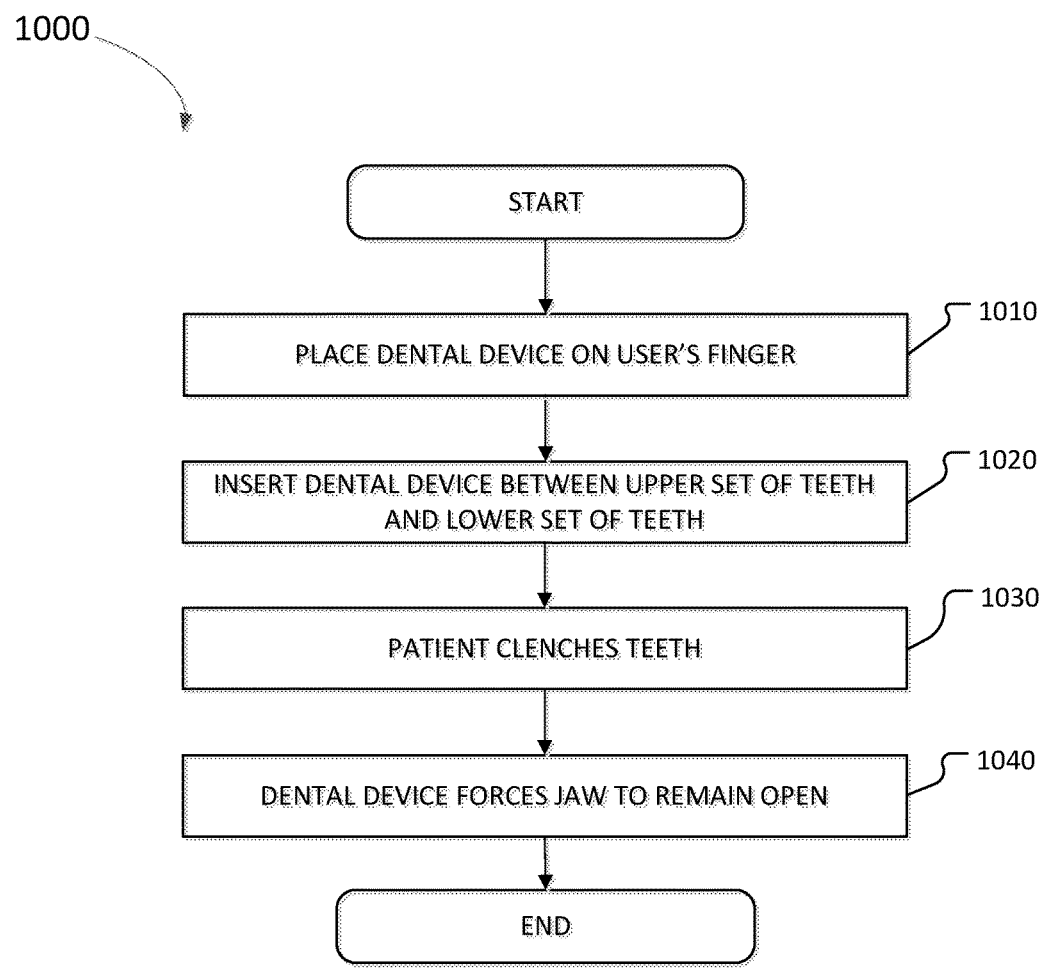
FIG. 10 depicts a method of using a dental device, according to an embodiment.
Figure 11:
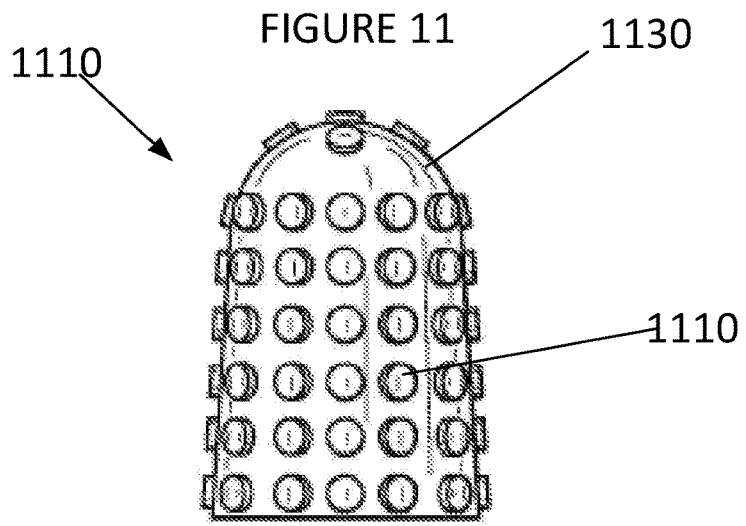
FIG. 11 depicts a front view of a dental device, according to an embodiment.
Figure 12:
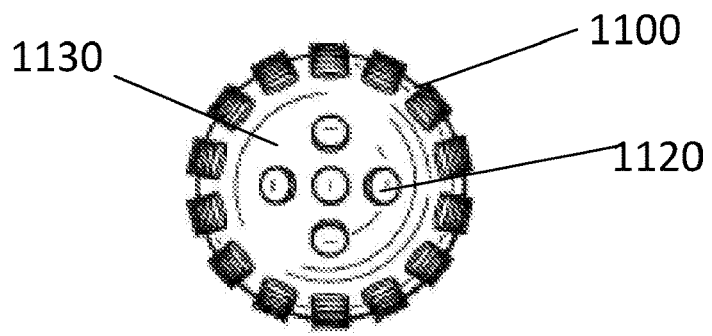
FIG. 12 depicts a top view of a dental device, according to an embodiment.
Figure 13:
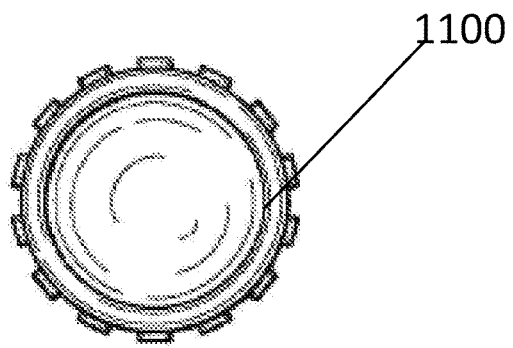
FIG. 13 depicts a bottom view of a dental device, according to an embodiment.
Figure 14:
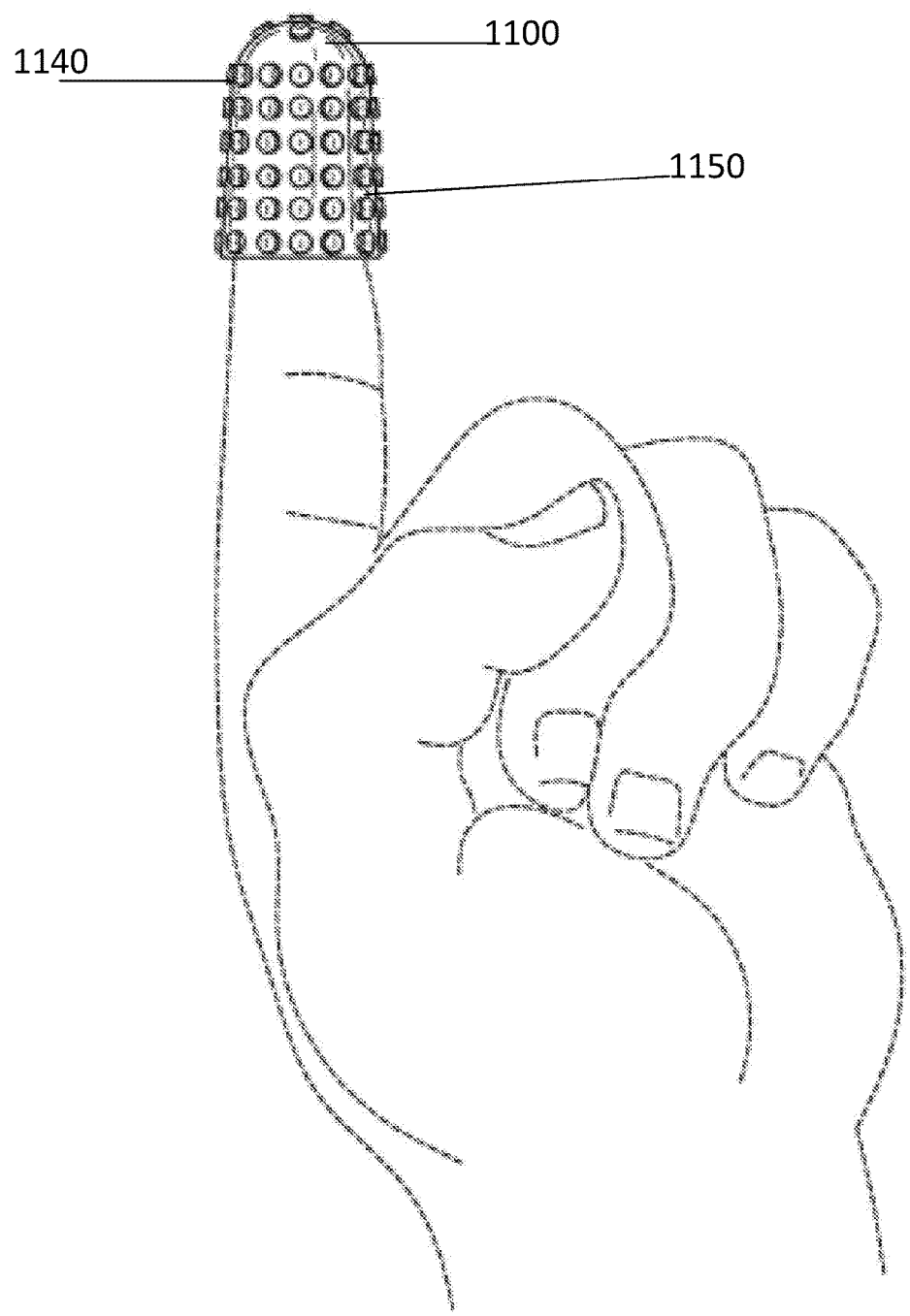
FIG. 14 depicts a dental device on a user's finger, according to an embodiment.
Figure 15:
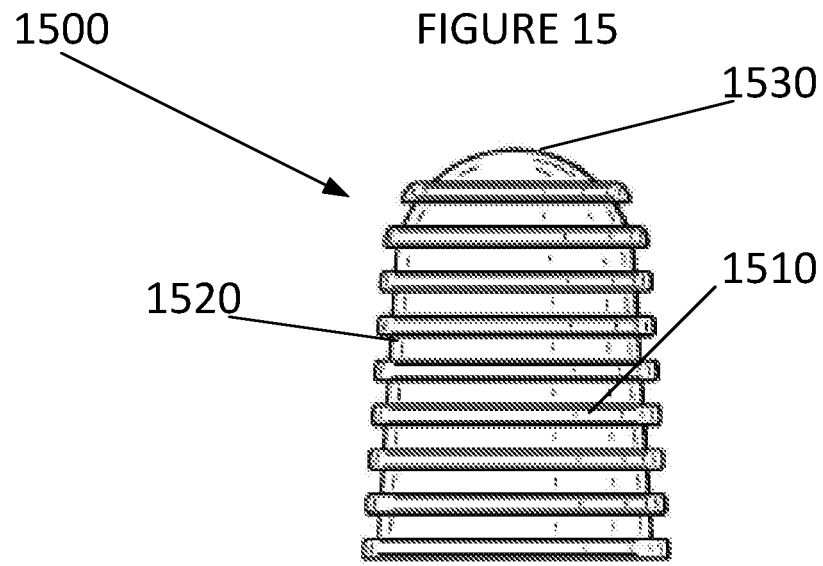
FIG. 15 depicts a front view of a dental device, according to an embodiment.
Figure 16:
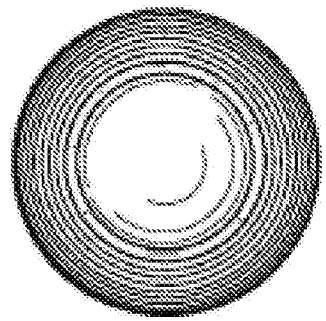
FIG. 16 depicts a top view of a dental device, according to an embodiment.
Figure 17:
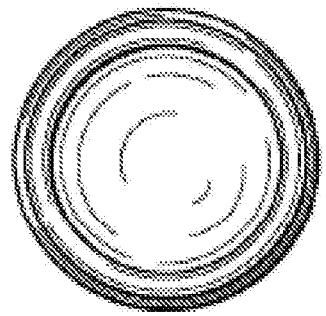
FIG. 17 depicts a bottom view of a dental device, according to an embodiment.
Figure 18:
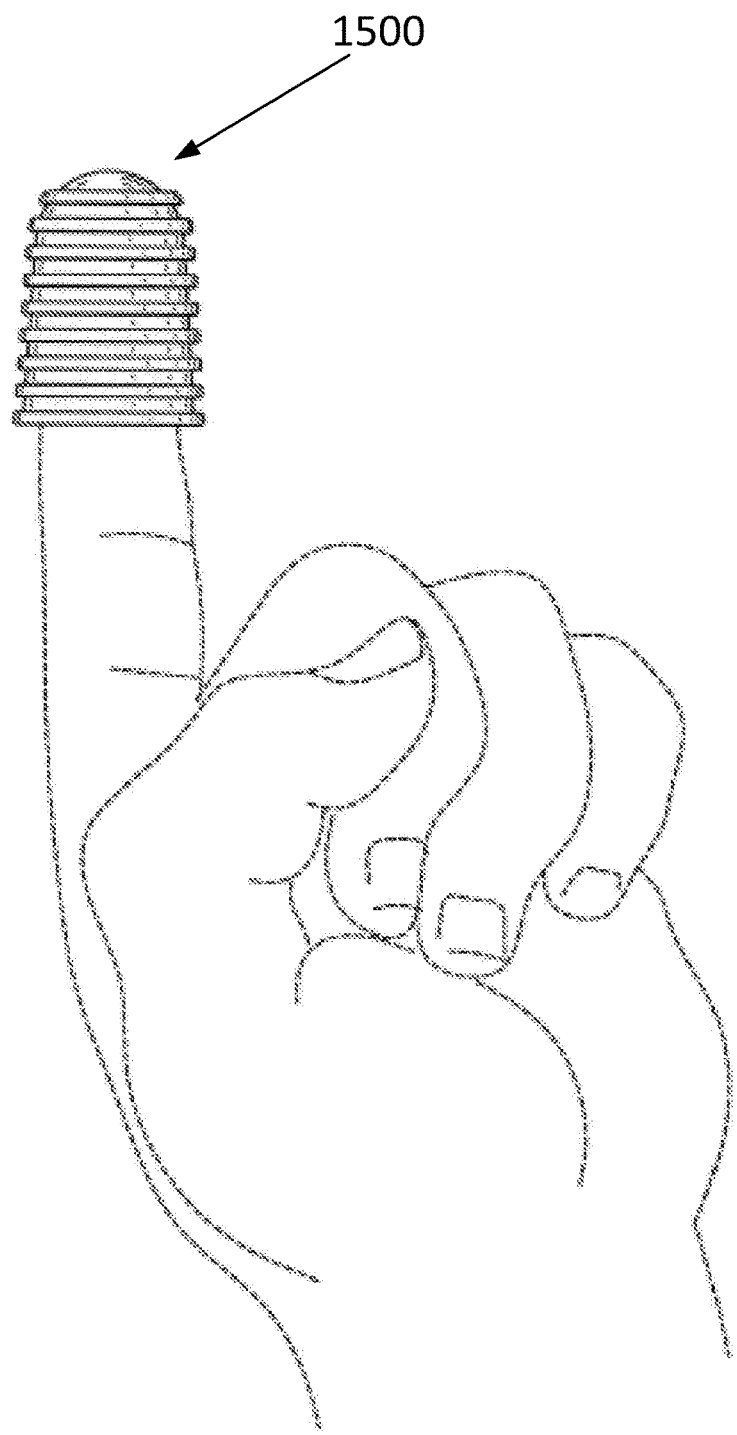
FIG. 18 depicts a dental device on a user's finger, according to an embodiment.

FIG. 10 illustrates a method 1000 for utilizing a utilizing a dental device to brush the teeth of a patient. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

At operation 1010, a user may position their finger through an open end of a dental device. The user's finger may be inserted through a hollow chamber within the dental device, until the distal end of the finger is proximate to a second, closed end of the dental device.

At operation 1020, the user may insert their finger covered by the dental device within a mouth of a patient. The dental device may be positioned between an upper set of teeth and a lower set of teeth of the patient.

At operation 1030, the patient may clench their teeth. When clenching their teeth, the patient's upper set of teeth and lower set of teeth may produce forces towards each other.

At operation 1040, due to the rigidity and/or semi-rigidity of the dental device, the patient may not be able to close their jaw, even when clenching their teeth. More specifically, the distance between the patient's upper set of teeth and lower set of teeth may be a fixed diameter corresponding to the diameter of the dental device.

FIGS. 11-14 depicts a dental device 1100, according to an embodiment. As depicted in FIGS. 11-14, dental device 1100 may have a plurality of projections 1110 extending away from an exterior surface of dental device 1100. The plurality of projections 1110 may be uniform bumps, ridges, humps, etc. The projections 1110 may form a plurality of columns that are evenly spaced apart, and a plurality of rows that are slightly offset due to the tapered sidewalls of dental device 1100. The slight offset may be configured to allow sets of teeth with different s to sit between different rows of projections 1110.

In embodiments, the second end of dental device may include a second set of plurality of projections 1120, wherein there is a channel 1130 between plurality of projections 1110 and the second set of projections 1120.

As further depicted in FIGS. 11-14, a top surface 1140 of dental device 1100 may be substantially linear, whereas a lower surface 1150 of dental device 1100 may be tapered and include a concave curve, which may correspond to the curvature of the user's finger.

FIGS. 15-18 depicts a dental device 1500 with ridges 1510 and channels 1520. In embodiments the width of ridges 1510 may remain fixed, while the distance between channels 1520 may decrease from the first end of dental device 1500 towards the second end of dental device 1500. The differences in widths of channels 1520 may allow for different sized teeth to be inserted within the channels 1520.

As further depicted in FIGS. 15-18, there may be not ridges on the second end 1530 of dental device 1500. The may enable a rounded, smoother surface to be inserted into the mouth of the patient, which may increase the comfort level of the patient.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

The flowcharts and block diagrams in the flow diagrams illustrate the architecture, functionality, and operation of possible implementations of systems, methods, and computer program products according to various embodiments of the present embodiments.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

What is claimed is:

1. A dental device comprising:
a housing with an open first end, a closed second end and an outer surface, the housing being comprised of rigid materials, wherein the outer surface of the closed second end is rounded and a tip for the dental device is positioned on the closed second end;

a hollow opening extending from the open first end towards the closed second end, the hollow opening being configured to receive a finger of a user;

tapered internal sidewalls within the hollow opening configured to secure the dental device to the finger of a user, wherein a circumference of the housing decreases from the open first end towards the closed second end;

and a first set of rigid projections being in a plurality of rows positioned on a first portion of the housing around an entire border of the outer surface of the housing, the first set of rigid projections being configured to secure the housing between an upper set of teeth and a lower set of teeth, wherein the first set of rigid projections are non-continuous bumps on the outer surface of the housing, wherein a first distance between each of the rows of projections positioned on the first portion of the housing are each separated by a first length;

a second set of rigid projections positioned on a second portion of the housing, the second set of rigid projections including a first rigid projection positioned on an apex of the closed second end and including only four other rigid projections, the only four other rigid projections are positioned ninety degrees apart from each other on the closed second end with respect to the first rigid projection; and a channel separating the first set of rigid projections from the second set of rigid projections, the channel is sized to receive different sized teeth between the first set of rigid projections and the second set of rigid projections, the channel having a second distance, the second distance extending across the channel from the first set of rigid projections to the second set of rigid projections, the second distance being greater than the first distance;

a lower exterior surface of the outer surface of the housing that extends from the open first end to the closed second end, the lower exterior surface including a continuously convexly curved perimeter that continuously and uniformly tapers and gradually decreases an outer diameter of the dental device from an edge of the open first end to the closed second end, the lower exterior surface extending across the first set of rigid projections and the second set of rigid projections, wherein the first set of rigid projections are positioned adjacent to the edge of the open first end to the channel.

2. The dental device of claim 1, wherein the projections are cylindrical in shape.

3. The dental device of claim 1, wherein each of the rows projections positioned on the first portion of the housing includes a same number of projections.

4. The dental device of claim 3, wherein a spacing between each of the projections on different rows is greater closer to the open first end.

* * * * *